(12) United States Patent
Pan et al.

(10) Patent No.: US 10,390,919 B2
(45) Date of Patent: Aug. 27, 2019

(54) INSPECTION APPARATUS FOR OSSEOINTEGRATION OF IMPLANTS

(71) Applicant: NATIONAL CENTRAL UNIVERSITY, Taoyuan (TW)

(72) Inventors: Min-Chun Pan, Taoyuan (TW); Chin-Sung Chen, Taipei (TW); Shiou-Bair Lin, Taipei (TW); Shih-Yao Wang, Taipei (TW); Jhao-Ming Yu, Taichung (TW)

(73) Assignee: National Central University, Taoyuan (TW)

( * ) Notice: Subject to any disclaimer, the term of this patent is extended or adjusted under 35 U.S.C. 154(b) by 205 days.

(21) Appl. No.: 15/454,264

(22) Filed: Mar. 9, 2017

(65) Prior Publication Data

US 2018/0064517 A1  Mar. 8, 2018

(30) Foreign Application Priority Data

Sep. 2, 2016  (TW) .............................. 105128537 A (51) Int. Cl.
*G01N 29/24* (2006.01)
*G01N 29/04* (2006.01)
(Continued)

(52) U.S. Cl.
CPC ............ *A61C 19/04* (2013.01); *A61B 5/0051* (2013.01); *A61B 5/0534* (2013.01);
(Continued)

(58) Field of Classification Search
CPC ... A61B 5/0051; A61B 5/0534; A61B 5/0088; G01N 29/2406; G01N 29/043; G01N 29/2418; A61C 8/0006; A61C 19/04
(Continued)

(56) References Cited

U.S. PATENT DOCUMENTS 8,167,614 B2 *  5/2012  Pan .................... A61B 5/1111
433/72
8,974,389 B2 *  3/2015  Pan .................... A61B 5/4542
433/119

(Continued)

OTHER PUBLICATIONS

Min-Chun Pan, Shiou-Bair Lin, Shih-Yao Wang, Jhao-Ming Yu, Chin-Sung Chen, "Osseointegration Detection Device for Dental Implantation", Exhibition Information, May 31, 2015, Taiwan, R.O.C.

*Primary Examiner* — Jacques M Saint Surin
(74) *Attorney, Agent, or Firm* — Rosenberg, Klein & Lee (57) ABSTRACT

The present invention provides an inspection apparatus for osseointegration of implants, which comprises an inspection base, a holding end, and an inspection end. The holding end is disposed at one end of the inspection base; the inspection end is disposed at the other end of the inspection base. Beside, the inspection end is disposed on one side of the holding end. The holding end includes a signal processing module and a wireless transmission module therein. The inspection end includes an inspection probe, disposed at one end of the inspection end. The inspection probe includes one or more excitation device and a receiver located on the same side of the inspection probe. According to the present invention, the inspection apparatus detects the condition of an object under inspection in a non-contact manner by using an excitation source. An acquired displacement difference is then transmitted to an electronic apparatus through wireless transmission.

10 Claims, 4 Drawing Sheets

(51) Int. Cl.
  *A61B 5/00*   (2006.01)
  *A61B 5/053*  (2006.01)
  *A61C 8/02*   (2006.01)
  *A61C 19/04*  (2006.01)

(52) U.S. Cl.
  CPC ......... *A61C 8/0006* (2013.01); *G01N 29/043* (2013.01); *G01N 29/2406* (2013.01); *G01N 29/2418* (2013.01); *A61B 5/0088* (2013.01)

(58) Field of Classification Search
  USPC .......................................................... 73/602
  See application file for complete search history.

(56) References Cited

U.S. PATENT DOCUMENTS

| | | | |
|---|---|---|---|
| 8,979,758 B2 * | 3/2015 | Stein ................... | A61B 5/0031 600/438 |
| 2007/0089518 A1 * | 4/2007 | Ericson .................... | A61F 2/30 73/649 |

* cited by examiner

INSPECTION APPARATUS FOR OSSEOINTEGRATION OF IMPLANTS

FIELD OF THE INVENTION

The present invention relates generally to an inspection apparatus for osseointegration of implants, and particularly to an inspection apparatus capable of inspecting the osseointegration condition of implants by a non-contact method and transmitting wirelessly quantified inspection data to related equipment.

BACKGROUND OF THE INVENTION

Osseointegration means the combination relation between an implant and the alveolar bone. After an implant is implanted into the alveolar bone, the bone tissue will combine tightly with the implant following the processes of bone cells contacting the implant, adhesion, healing, and calcification on the surface of the implant. In clinical practices, due to the slow process of osseointegration for implants, constant observations and diagnoses of patients' post-surgical conditions by doctors are required for recording and evaluating the osseointegration condition of implants in respective treatment stages.

According to the Taiwan Patent Publication Number I365736, an inspection apparatus for irregular bone defects in dental implants is disclosed. Please refer to FIG. 1, which shows a schematic diagram of the inspection apparatus for irregular bone defects in dental implants according to the prior art. Please refer to pages 10 to 15 in the Detailed Description of the specifications of the invention I365736: "The inspection apparatus for dental implants 1 according to the present invention comprises a metal extension 11, an inspection probe 12, a transducer and inspector driver 13, and an inspection instrument 14. The metal extension 11 is a pillar structure made of anti-erosive metal materials with threads at the bottom for being fastened and attached to a dental implant . . . . The inspection probe 12 includes a non-contact sound transducer at the actuating end and a responding micro accelerometer. The inspection probe 12 covers the metal extension 11 for actuating the structure and receiving the response. By using the miniature non-contact sound transducer and the micro accelerometer, the measurement and evaluation for oral cavities can be performed with ease. The inspection probe 12 can also cover directly the protruding part of the connecting body of various dental implants with the non-contact sound transducer inside the probe not contacting the dental implants. The size of the inspection probe 12 can be adjusted according to the dental implants or the metal extension 11. Besides, different inspection probes 12 can be disassembled and replaced according to the requirement in inspection accuracy. One end of the transducer and inspector driver 13 is connected with the inspection probe 12, while the other end thereof is connected with the inspection instrument 14 via a signal wire 21. The inspection instrument 14 is connected with a personal computer 15 via a USB wire 22. The inspection instrument 14 is formed by a liquid crystal display 141, an acoustic excitation generator 142, a structure response-receiving and frequency-analyzing device 143, a processor 144, a memory 145, and a button control device 146. The personal computer 15 transmits measurement data through the USB wire 22. In addition, the inspection instrument 14 can be controlled via the computer operating interface for measurement."

Figure 1:
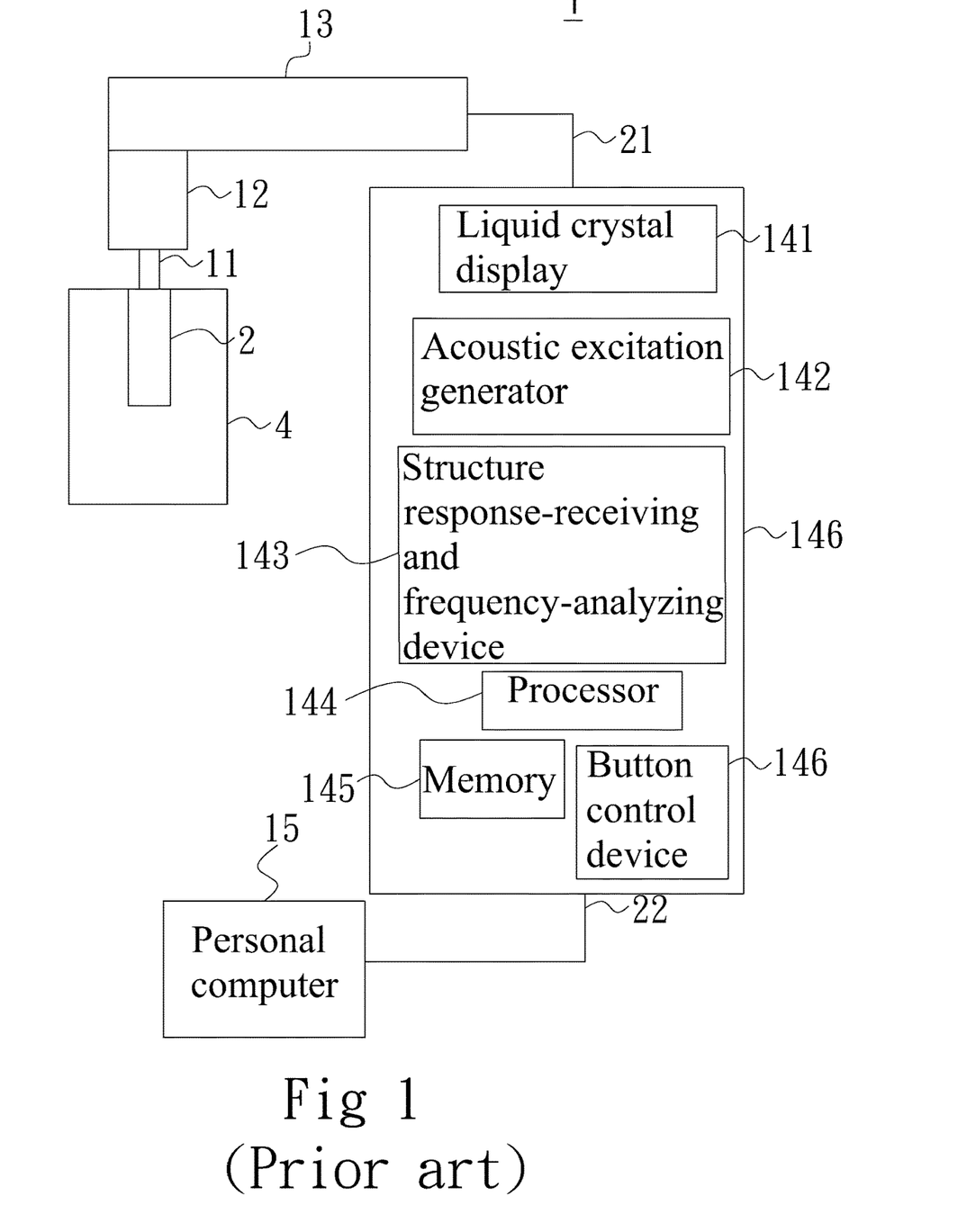
FIG. 1 shows a schematic diagram of the inspection apparatus for irregular bone defects in dental implants according to the prior art.

According to the prior art as described above, the personal computer 15 is used for controlling the operation of the inspection instrument 14. By using the acoustic excitation generator 142 and the transducer and inspector driver 13, the non-contact sound transducer generates non-contact acoustic waves to excite the metal extension 11. Then, the micro accelerometers inside the inspection probes 12 are used to receive the excitation and generate structure vibration signals. The transducer and inspector driver 13 transmits the vibration signals to the structure response-receiving and frequency-analyzing device 143 in the inspection instrument 14 for further analysis and process.

After processing, the resonance frequencies in the respective directions of the micro accelerometers can be given. The calculated data are then displayed on the liquid crystal display 141 and stored in the memory 145. Besides, the data can be transmitted to the personal computer 15 for managing the reports for the testees.

The technology according to the prior art as described above still has the following drawbacks:

1. It is required to fasten the metal extension according to the prior art to the dental implant. Alternatively, the inspection probe should cover the protruding part of the connecting body of various dental implants before inspecting implant bones.
2. After inspecting implant bones according to the prior art, it is required to connect the transducer and inspector driver to the inspection instrument using the signal wire. Alternatively, the transducer and inspector driver should connect to the inspection instrument directly before the inspection data can be displayed on the liquid crystal display. The other way is to connect the inspection instrument to the personal computer using the USB wire and view the inspection data on the personal computer.
3. The size of the metal extension according to the prior art should be adjusted according to various dental implants. The size of the inspection probe should be adjusted according the dental implants or the metal extension before inspection of implants can be performed.

Accordingly, the inspection apparatus for osseointegration of implants according to the prior art still needs to be improved. It has become an important direction for the industry to solve the problems as well as improving the structure.

Hence, the present invention provides an inspection apparatus for osseointegration of implants for improving the usage convenience, enhancing inspection accuracy, and bringing economic benefits in the hope of serving people and promoting the development of the industry.

SUMMARY

An objective of the present invention is to provide an inspection apparatus for osseointegration of implants. By using the inspection apparatus for osseointegration of implants, the osseointegration condition of implants can be inspected without contacting an object under inspection. The inspection apparatus according to the present invention can also inspect the stability of osseointegration, the bone loss, the position of bone loss, and the depth of bone loss.

Another objective of the present invention is to provide an inspection apparatus for osseointegration of implants. Because no contact is required while inspecting the osseointegration condition of implants, the size of the object under inspection can be arbitrary. There is no matching problem.

Still another objective of the present invention is to provide an inspection apparatus for osseointegration of implants. The inspection data can be transmitted through a wireless transmission module for displaying on a display device or storing in a central processing unit. Hence, transmission wires and the problem of equipment connection can be simplified.

Still another objective of the present invention is to provide an inspection apparatus for osseointegration of implants, which further comprises a flexible and retractable rod. One end of the flexible and retractable rod passes through the holding end; the other end thereof is connected with the inspection probe and pivoted movably at the inspection end. Thereby, the user can bend the flexible and retractable rod according to the field requirement for adjusting the angle of the inspection probe. Alternatively, the flexible and retractable rod can be elongated for extending the length of the inspection probe and thus satisfying ergonomic requirements.

A further objective of the present invention is to provide an inspection apparatus for osseointegration of implants, which further comprises an adjusting device, a connecting rod, and a support device. The adjusting device is pivoted at the inspection end. One end of the connecting rod is pivoted on one side of the adjusting device while the other end thereof is connected to the support device. By pivoting the adjusting device or the support device during inspection using the inspection apparatus according to the present invention, the inspection device can be positioned and supported at an arbitrary position in the patient's oral cavity by the adjusted support device for facilitating inspection.

In order to achieve the above objectives and efficacies, the present invention provides an inspection apparatus for osseointegration of implants, which comprises an inspection base, a holding end, and an inspection end. The holding end is disposed at one end of the inspection base; the inspection end is disposed at the other end of the inspection base. Beside, the inspection end is disposed on one side of the holding end. The holding end further includes a signal processing module and a wireless transmission module therein. The inspection end further includes an inspection probe, disposed at one end of the inspection end. The inspection probe further includes one or more excitation device and a receiver located on the same side of the inspection probe. The signal processing module, the wireless transmission module, the excitation device, and the receiver are connected electrically to one another. According to the present invention, the inspection apparatus approaches an object under inspection. The excitation device of the inspection probe generates an excitation source to vibrate the object under inspection in a non-contact manner. Meanwhile, the receiver receives the vibration response signal of the object under inspection. Afterwards, the signal processing module analyzes the vibration response signal and gives a displacement difference. The displacement difference is transmitted via the wireless transmission module to a display device for displaying or to a central processing unit for storage. Accordingly, the operational convenience of the inspection apparatus for osseointegration of implants according to the prior art can be simplified. In addition, the transmission lines can be omitted and the complexity of equipment connection can be simplified; the accuracy of inspection results can be improved.

DETAILED DESCRIPTION

In order to make the structure and characteristics as well as the effectiveness of the present invention to be further understood and recognized, the detailed description of the present invention is provided as follows along with embodiments and accompanying figures.

Figure 2:
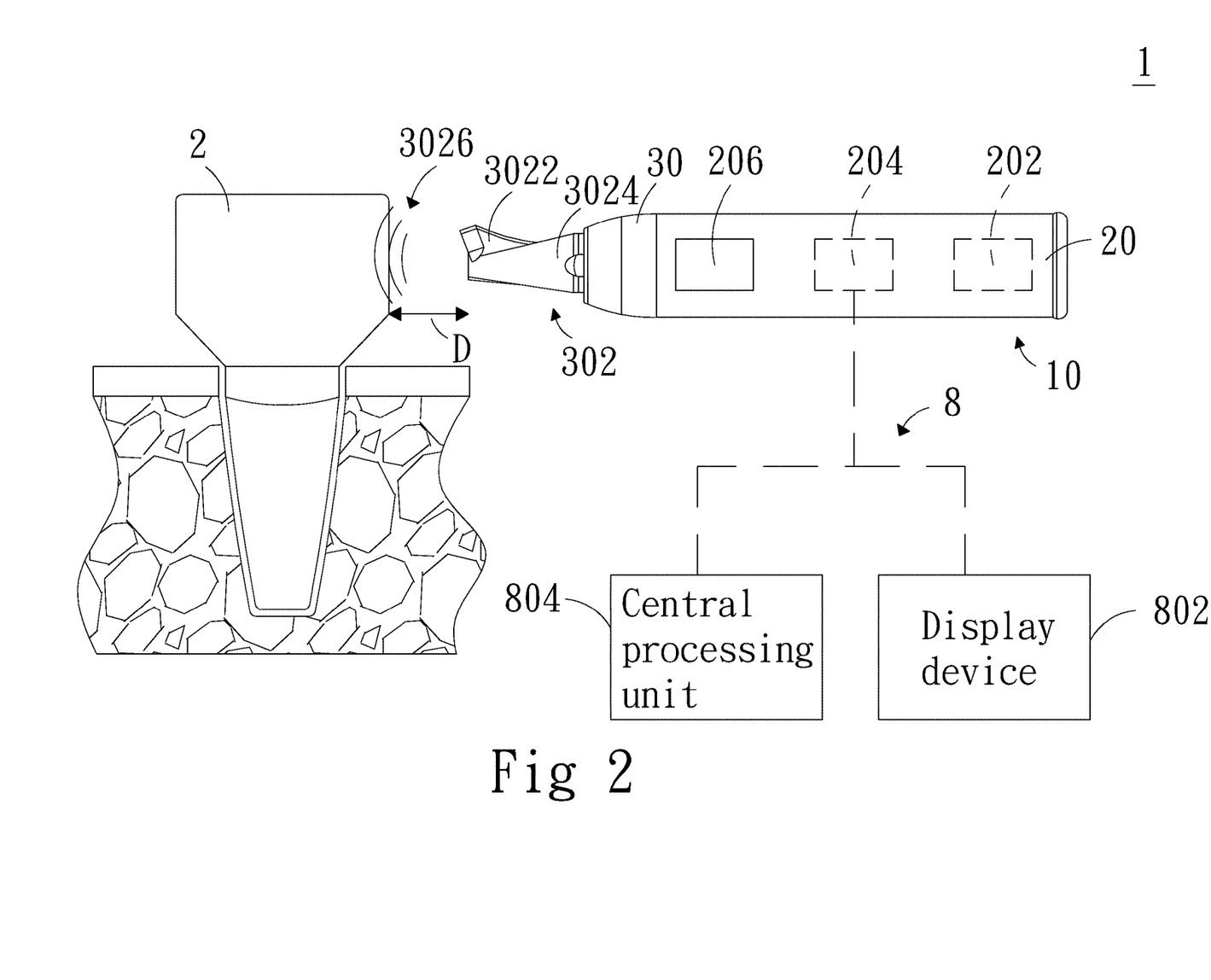
FIG. 2 shows a schematic diagram of the operations of the inspection apparatus for osseointegration of implants according to the first embodiment of the present invention.

Please refer to FIG. 2, which shows a schematic diagram of the operations of the inspection apparatus for osseointegration of implants according to the first embodiment of the present invention. As shown in the figure, the inspection apparatus for osseointegration of implants 1 according to the present invention comprises an inspection base 10, a holding end 20, and an inspection end 30. The holding end 20 is disposed at one end of the inspection base 10, and further includes a signal processing module 202 and a wireless transmission module 204. The signal processing module 202 and the wireless transmission module 204 are disposed inside the holding end 20. In addition, the signal processing module 202 and the wireless transmission module 204 are connected electrically. The inspection end 30 is disposed at the other end of the inspection base 10 and on one side of the holding end 20. The inspection end 30 further includes one or more excitation device 3022 and a receiver 3024. The excitation device 3022 and the receiver 3024 are located on the same side of the inspection probe 302 and connected electrically to the signal processing module 202. The inspection apparatus 1 approaches an object under inspection 2. The signal processing module 202 enables the excitation device 3022 to generate an excitation source with a frequency range. The object under inspection 2 is vibrated in a non-contact manner. Meanwhile, the receiver 3024 receives the vibration response signal of the object under inspection 2. Afterwards, the signal processing module 202 analyzes the vibration response signal and gives a displacement difference (not shown in the figure). The displacement difference is transmitted via the wireless transmission module 204 to an electronic apparatus 8.

The inspection apparatus 1 according to the present invention can be a handheld inspection apparatus 1. Alternatively, by integrating with a dental chair, the inspection apparatus 1 according to the present invention can be combined with a mechanical arm (not shown in the figure) for performing inspection. When the inspection probe 302 approaches the object under inspection 2, the inspection probe 302 maintains a distance D with the object under inspection 2. At this moment, the excitation device 3022 is activated to emit broad-band excitation waves in the acoustic form with a frequency range between 200 and 10000 Hz and enable the object under inspection 2 to vibrate. At the same time, the receiver 3024 located on the same side of the inspection probe 302 extracts the vibration response signal of the object under inspection 2. By same-side excitation and sensing the object under inspection 2, the instantaneous integration condition of the object under inspection 2 can be given more effectively. Afterwards, the signal processing module 202 analyzes the vibration response signal fed by the receiver 3024 and calculates the displacement difference between the object under inspection 2 and the implant environment. The displacement difference is transmitted to the related electronic equipment 8 and interface via the wireless transmission module 204. Then the integration condition of the object under inspection 2 and the implant environment can be diagnosed.

The object under inspection 2 is an abutment or a tooth. To observe the integration condition of the object under inspection 2 is to record and evaluate the osseointegration variations of the abutment or the tooth in various treatment stages for the doctor to provide prompt interventions. In addition, the receiver 3024 is a noncontact sensor for measuring vibration response signals as capacitive and optical type. The selection depends on the condition of the inspection field for maintaining the accuracy of inspecting the osseointegration condition of implants. Besides, the excitation device 3022 can be a micro sound guide used for transmitting an excitation sound source.

The excitation device 3022 according to the present invention can emit an excitation source 3026, which contains broad-band sound waves in the acoustic form with a frequency range between 200 and 10000 Hz. Meanwhile, the receiver 3024 receives the vibration response signal of the object under inspection 2 simultaneously. The signal processing module 202 analyzes to give the displacement difference information such as the stability of osseointegration, the bone loss, the position of bone loss, and the depth of bone loss. The resonance frequency analysis is a method to quantify the osseointegration condition of implants. The method mainly takes advantage of the resonance phenomenon of objects to give the contact relation between the abutment/tooth and the surrounding bone. Thereby, the factors affecting osseointegration can be understood.

The receiver 3024 collects the vibration response signal excited by the excitation source 3026, which is applied by the excitation device 3022 on the object under inspection 2. The signal processing module 202 analyzes and records the amplitude variation for the object under inspection 2 and the surrounding bone, and thus giving the junction condition between the abutment/tooth and the surrounding bone. This is distinct from current clinical X-ray observation method. In the latter method, a patient is first led to an X-ray scanner for scanning and analysis. Next, a doctor evaluates the osseointegration condition according to the scanning result. Unfortunately, the method has the shortcomings of inability in judging patients' healing condition promptly as a result of operating environment limitation, limits of two-dimensional X-ray image information, and difficulty in quantification.

Please refer again to FIG. 2. The inspection apparatus 1 according to the present invention can further include a control module 206 outside the holding end 20. The control module 206 is connected electrically with the signal processing module 202, the wireless transmission module 204, the excitation device 3022, and the receiver 3024. The control module 206 can operate the excitation device 3022, control the operation of the receiver 3024, and moderating the signal processing module 202 to enable the excitation device 3022 to emit the frequency range (200 to 10000 Hz) of the excitation source 3026. In addition, the control module 206 can transmit the data analyzed by the signal processing module 202 to a display device 802 for displaying via the wireless transmission module 204 or to a central processing unit 804 for storage. Moreover, the signal processing module 202 can also coordinate with a memory (not shown in the figure). The analyzed data can be first stored in the memory. Then, according to a user' operation, the quantified message is uploaded to the display device 802 or the central processing unit 804.

The wireless transmission module 204 performs transmission by infrared, Bluetooth, Wi-Fi, ANT, or ZIGBEE. The display device 802 can be a human-machine interface such as a screen, a smart mobile device, a computer, a tablet computer. The central processing unit 804 can be a cloud platform for a remote server for storing case histories.

Figure 3:
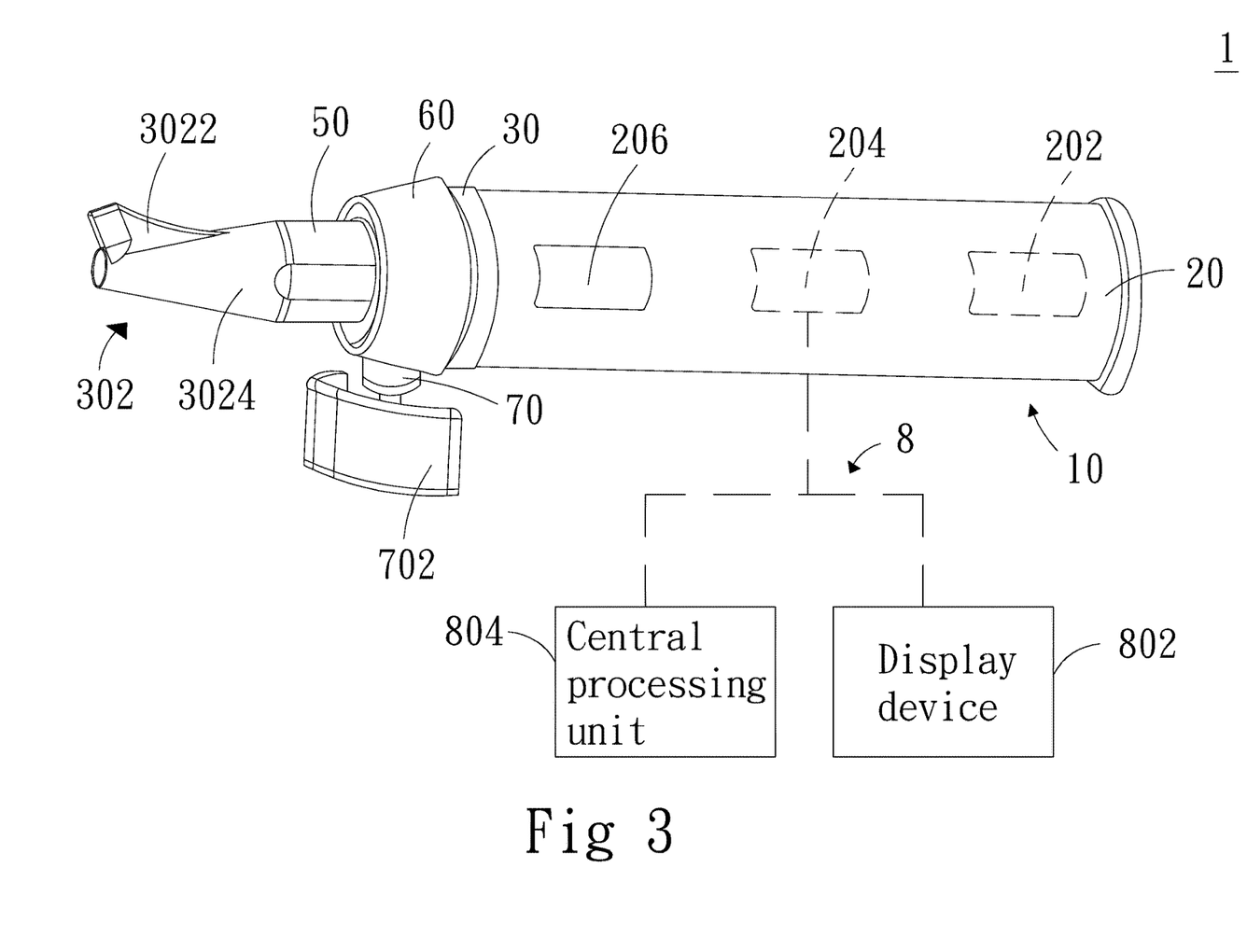
FIG. 3 shows a schematic diagram of the inspection apparatus for osseointegration of implants according to the second embodiment of the present invention.
Figure 4:
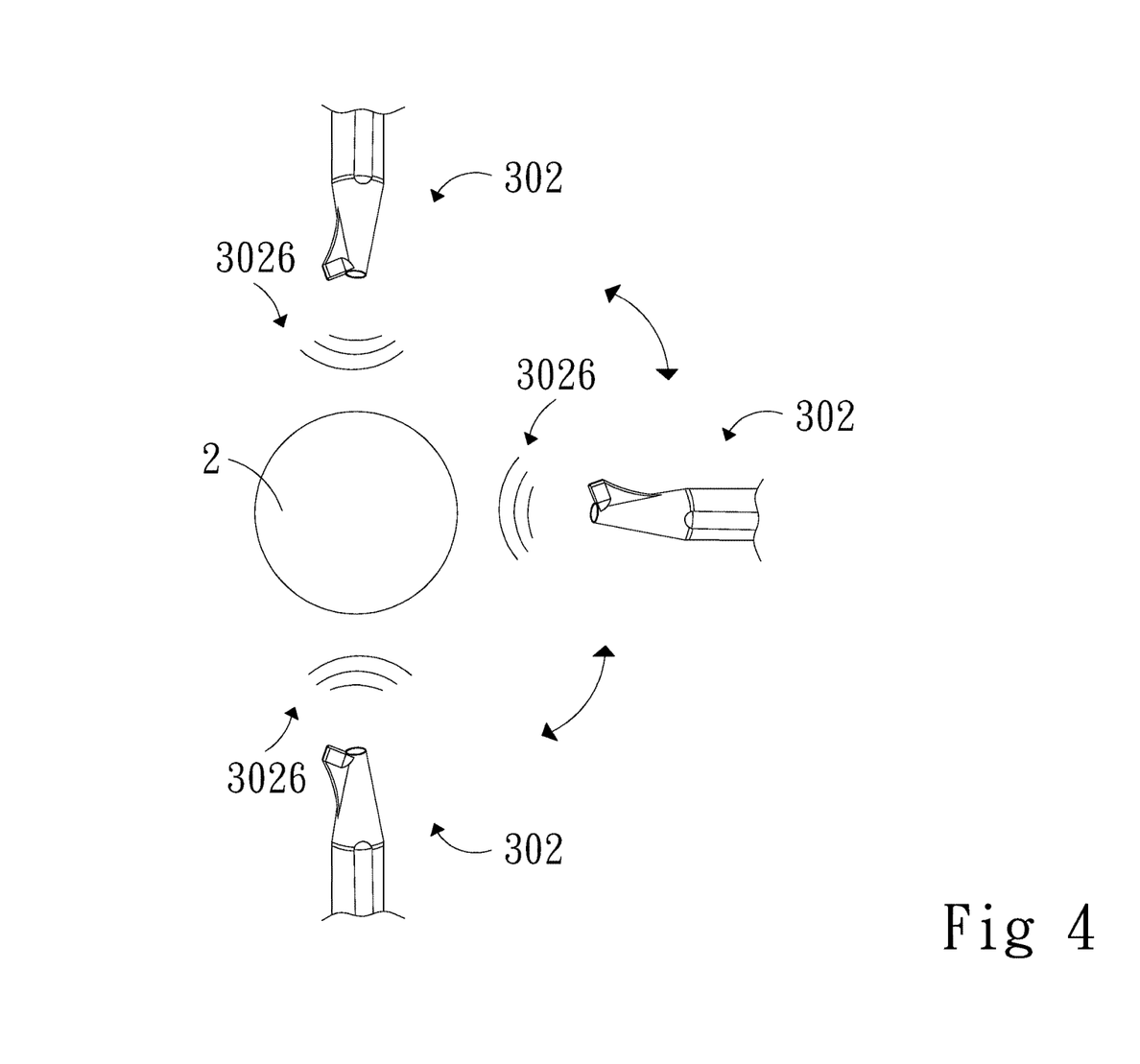
FIG. 4 shows a schematic diagram of the operations of the inspection apparatus for osseointegration of implants according to the second embodiment of the present invention.

Please refer to FIG. 3 and FIG. 4, which show a schematic diagram of the inspection apparatus and a schematic diagram of the operations for osseointegration of implants according to the second embodiment of the present invention. As shown in the figures, the inspection apparatus 1 according to the present invention further comprises a flexible and retractable rod 50. One end of the flexible and retractable rod 50 passes through the holding end 20; the other end thereof is connected with the inspection probe 302 and pivoted movably at the inspection end 30. By taking advantage of the retractable property of the flexible and retractable rod 50, the flexible and retractable rod 50 can be retrieved into the holding end 20 or elongated and thus extending the inspection probe 302 to the direction opposite to the holding end 20. Besides, according to the flexible property of the flexible and retractable rod 50, the flexible and retractable rod 50 can be bent and driving the angle of the inspection probe 302 to be changed. The object under inspection 2 can be implanted to an arbitrary position in patient's oral cavity depending on his illness condition. Thereby, a user can bend the flexible and retractable rod 50 according to the requirement of the inspection environment for adjusting the angle of the inspection probe 302, or extend the length of the inspection probe 302 for facilitating the inspection operation for osseointegration of implants. The flexible and retractable rod 50 owns the functions of adjusting angle and length for complying with ergonomic considerations. The inspection apparatus 1 according to the second embodiment of the present invention can provide the excitation source 3026 in different directions for vibrating the object under inspection 2, so that the receiver 3024 can receive the feedback vibration frequency signal from the object under inspection 2. Consequently, the signal processing module 202 can analyze and give more complete monitoring data, including the stability of osseointegration, the bone loss, the position of bone loss, or the depth of bone loss. The bending/extending operations of the flexible and retractable rod 50 can be adjusted manually or using the control module 206.

Moreover, the inspection apparatus 1 according to the present invention further comprises an adjusting device 60, a connecting rod 70, and a support device 702. The adjusting device 60 is pivoted on the inspection end 30. One end of the connecting rod 70 is pivoted on one side of the adjusting device 60 while the other end thereof is connected to the support device 702. As shown in FIG. 4, by pivoting the adjusting device 60, the connecting rod 70 will be driven to rotate. The support device 702 surrounds the inspection probe 302 and moves vertically around the circumference. By pivoting the support device 702, it can be driven to move horizontally around the circumference with respect to the inspection probe 302. Accordingly, when the user operates the inspection apparatus 1 for inspecting the osseointegration condition of implants, the support device 702 with an adjusted angle can be positioned and supported at an arbitrary portion inside the patient's oral cavity for facilitating inspection. The method for rotating the adjusting device 60 and the support device 702 can be manual or using the control module 206.

To sum up, the inspection apparatus for osseointegration of implants according to the present invention has the following advantages:

1. It is not required for the inspection apparatus for osseointegration of implants according to the present invention to contact the object under inspection before inspection can be performed. The inspection information of the stability of osseointegration, the bone loss, the position of bone loss, and the depth of bone loss can be provided. This is different from current clinical practices, such as X-ray scans, palpation, and other noninvasive inspection methods, can only provide the information of the overall stability between an implant and the alveolar.
2. While performing inspection using the inspection apparatus for osseointegration of implants according to the present invention, it is not required to fasten the related accessories in advance to the object under inspection nor contacting the object under inspection. Thereby, it is suitable for objects under inspection with an arbitrary size. No matching problem occurs.
3. The inspection data are transmitted using the wireless transmission module to the display device for displaying or to the central processing unit for storage, further simplifying the transmission lines and the connection problem among related apparatuses.
4. Thanks to the structural design of the flexible and retractable rod according to the present invention, the angle and position of the inspection probe can be adjusted to meet ergonomic considerations and reduce the limits imposed by the inspection environment.
5. The disposition of the adjusting device, the connecting rod, and the support device is beneficial for positioning and supporting the inspection apparatus to an arbitrary position inside the patient's oral cavity for facilitating inspection.
6. The above embodiments and advantages are applied to inspection for oral implants. Nonetheless, the handheld inspection apparatus according to the present invention can also be applied to the related field concerning combination of human bones with abutments. Alternatively, the inspection apparatus according to the present invention can be coupled to related electronic equipment, such as a mechanical arm, for performing inspection of the osseointegration condition for objects under inspection.

The present invention is not limited to the disclosed embodiments.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. An inspection apparatus for osseointegration of implants, comprising:
    an inspection base;
    a holding end, disposed at one end of said inspection base, further including a signal processing module and a wireless transmission module disposed inside of said holding end, and said signal processing module connected electrically with said wireless transmission module; and
    an inspection end, disposed at the other end of said inspection base and on one side of said holding end, further including an inspection probe disposed at one of said inspection end, one end of said inspection probe including one or more excitation device and a receiver, said one or more excitation device and said receiver located on the same side of said inspection probe, and said excitation device and said receiver connected electrically with said signal processing module;
    where said inspection apparatus approaches an object under inspection; said signal processing module enables said excitation device to generate an excitation source to vibrate said object under inspection in a non-contact manner; meanwhile, said receiver receives the vibration response signal of said object under inspection; said signal processing module analyzes said vibration response signal and gives a displacement difference; and said wireless transmission module transmits said displacement difference to an electronic apparatus.

2. The inspection apparatus for osseointegration of implants of claim 1, further comprising a flexible and retractable rod, one end of said flexible and retractable rod passing through said holding end, and the other end of said flexible and retractable rod connected with said inspection probe and pivoted movably at said inspection end.

3. The inspection apparatus for osseointegration of implants of claim 2, further comprising an adjusting device, a connecting rod, and a support device, said adjusting device pivoted at said inspection end, one end of said connecting rod pivoted on one side of said adjusting device, and the other end of said connecting rod connected to said support device.

4. The inspection apparatus for osseointegration of implants of claim 1, further comprising a control module is disposed outside of said holding end; said control module is connected electrically with said signal processing module, said wireless transmission module, said excitation device, and said receiver; and said control module controls the operations of said signal processing module, said wireless transmission module, said excitation device, and said receiver.

5. The inspection apparatus for osseointegration of implants of claim 4, wherein said electronic apparatus is a display device; said control module operates said wireless transmission module for transmitting said displacement difference analyzed by said signal processing module to said display device.

6. The inspection apparatus for osseointegration of implants of claim 4, wherein said electronic apparatus is a central processing unit; said control module operates said wireless transmission module for transmitting said displacement difference analyzed by said signal processing module to said central processing unit.

7. The inspection apparatus for osseointegration of implants of claim 1, wherein said receiver is a noncontact sensor for measuring vibration response signals such as capacitive and optical type.

8. The inspection apparatus for osseointegration of implants of claim 1, wherein said excitation source emits broad-band excitation waves in the acoustic form with a frequency range between 200 and 10000 Hz.

9. The inspection apparatus for osseointegration of implants of claim 8, wherein said excitation device is a micro sound guide for transmitting an excitation sound source.

10. The inspection apparatus for osseointegration of implants of claim 1, wherein said object under inspection is an abutment or a tooth.

* * * * *